United States Patent
Decristoforo et al.

(10) Patent No.: US 6,825,345 B2
(45) Date of Patent: Nov. 30, 2004

(54) PROCESS FOR PURIFICATION OF A CEPHALOSPORIN DERIVATIVE

(75) Inventors: Martin Decristoforo, Wattens (AT); Johannes Ludescher, Breitenbach (AT); Hubert Sturm, Innsbruck (AT); Werner Veit, Kufstein (AT)

(73) Assignee: Sandoz GmbH, Kundl (AT)

( * ) Notice: Subject to any disclaimer, the term of this patent is extended or adjusted under 35 U.S.C. 154(b) by 54 days.

(21) Appl. No.: 10/261,748

(22) Filed: Sep. 30, 2002

(65) Prior Publication Data

US 2003/0208065 A1 Nov. 6, 2003

Related U.S. Application Data

(63) Continuation of application No. 09/669,645, filed on Sep. 26, 2000, now abandoned, which is a continuation of application No. PCT/EP99/02222, filed on Mar. 31, 1999.

(30) Foreign Application Priority Data

Apr. 2, 1998 (AT) ................................. 575/98

(51) Int. Cl.$^7$ .......................................... C07D 501/22
(52) U.S. Cl. ...................................... 540/222
(58) Field of Search ......................... 540/222

(56) References Cited

U.S. PATENT DOCUMENTS

| 4,816,582 A | 3/1989 | Furlenmeier et al. ......... 417/12 |
| 5,359,057 A | 10/1994 | Furlenmeier et al. .......... 501/6 |

FOREIGN PATENT DOCUMENTS

| EP | 0 658 558 | 6/1995 |
| EP | 0 831 093 | 3/1998 |
| EP | 0 093 376 | 4/1999 |
| WO | WO 97/07121 | 2/1997 |
| WO | WO 98/06723 | 2/1998 |
| WO | WO 98/31685 | 7/1998 |

OTHER PUBLICATIONS

Yamanaka et al., Studies on beta–lactam antibiotics, Synthesis and biologigal activity of a new orally active cephalosporing, cefixime (FK027), The Journal of Antibiotics, pp 1738–1751 (1985).
International Search Report.

*Primary Examiner*—Mark L. Berch
(74) *Attorney, Agent, or Firm*—John D. Thallemer; Diane E. Furman

(57) ABSTRACT

A process for the purification of cefixime via a novel tert-octylamine salt of a cefixime intermediate of formula V

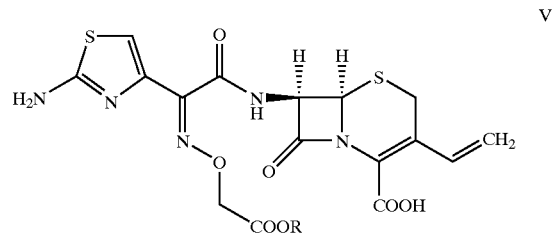

which may be crystalline and which may be produced in a one-pot reaction from 7-amino-3-vinyl-ceph-3-em-4-carboxylic acid.

13 Claims, No Drawings

PROCESS FOR PURIFICATION OF A CEPHALOSPORIN DERIVATIVE

This is a continuation of U.S. application U.S. Ser. No. 09/669,645, filed Sep. 26, 2000, now abandoned; which in turn a continuation of International Application No. PCT/EP99/02222, filed Mar. 31, 1999.

The present invention relates to a process for the purification of 7-[2-[aminothiazol-4-yl)-2-[(carboxymethoxyimino)acetamido]-3-vinyl-3-ceph-3-em-4-carboxylic acid, e.g. cefixime of formula

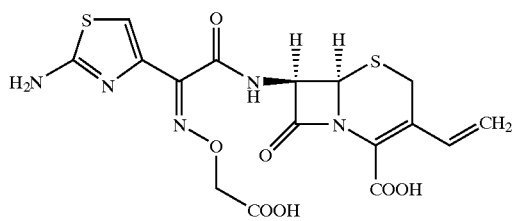

II

Cefixime, e.g. in the form of a trihydrate, is a cephalosporin antibiotic with excellent antibacterial properties and high β-lactamase stability (see for example H. Yamanaka et al., J.Antibiotics (1985), 38(12), p 1738–1751).

Cefixim may be prepared via a 7-{2-[(2-aminothiazol)-4-yl]-2-[((aryl-or alk)-oxy-carbonyl)-methoxyimino]acetamido}-3-vinyl-ceph-3-em-4-carboxylic acid, which may be prepared according to a novel process.

In one aspect the present invention provides a process for the production of a compound of formula

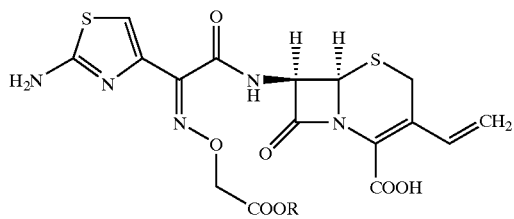

V wherein R denotes alkyl or aryl and wherein the amine group attached to the thiazolyl ring is free or protected, comprising reacting a compound of formula

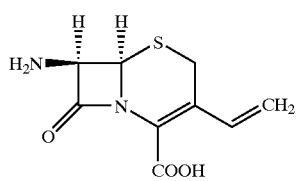

III in free form, protected form or in the form of a salt, with a compound of formula

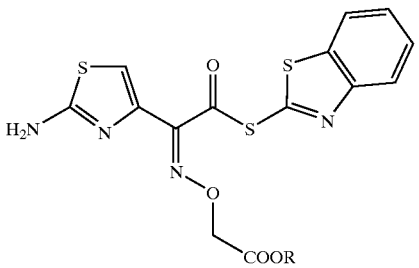

IV wherein R denotes alkyl or aryl and wherein the amine group attached to the thiazolyl ring is free or protected, and isolating a compound of formula V from the reaction mixture, e.g. optionally after splitting off protecting groups and/or converting a compound of formula V in the form of a salt into a compound of formula V in free form.

In formula IV and V R denotes alkyl, e.g. ($C_{1-8}$)alkyl, such as ($C_{1-4}$)alkyl, e.g. methyl, ethyl, propyl, isopropyl, butyl, or isobutyl; e.g. methyl; or aryl, e.g. phenyl, preferably alkyl. Alkyl and aryl may be unsubstituted or substituted, e.g. by groups which are inert under appropriate reaction conditions for the acylation of an amine group.

A compound of formula IV wherein R is methyl, ethyl, propyl, isopropyl, butyl, or isobutyl and wherein the amine group is free or protected is novel.

In another aspect the present invention provides a compound of formula IV wherein R is methyl, ethyl, propyl, isopropyl, butyl, or isobutyl and wherein the amine group attached to the thiazolyl ring is free or protected.

A process according to the present invention may be carried out as follows:

A compound of formula IV may e.g. be prepared by reaction of 2-(2-amino-4-thiazolyl)-(Z)-2-((aryl-or alk)-oxycarbonylmethoxyimino))acetic acid with 2,2'-benzothiazolyl disulphide in an organic solvent, e.g. dichloromethane in the presence of a phosphine, e.g. triphenylphosphine or a phosphite, e.g. triethyl phosphite, e.g. at room temperature. Protection groups of the amine group attached to the thiazolyl ring include protection groups which are conventional in β-lactam chemistry, e.g. protection groups as described below for the amine group attached in position 7 of the ring structure of a compound of formula III. Protection of the amine group may e.g. be carried out as conventional.

A compound of formula IV, e.g. produced as described above, e.g. without isolation from the reaction mixture, may be reacted with a compound of formula III. A compound of formula III may be in free form, in the form of a salt, e.g. in alkali salt form or in the form of a salt with ammonia, amines, such as a tertiary amines, e.g. trialkylamines, e.g. wherein the alkyl groups independently of each other each denote e.g. ($C_{1-8}$)alkyl, such as ($C_{1-4}$)alkyl e.g. triethylamine or tributylamine; amidines, e.g. DBN or DBU, or guanidines, e.g. tetramethyl guanidine, preferably triethylamine; or a compound of formula III may be in protected form, e.g. wherein functional groups such as the amine group in position 7 and/or the carboxyl group in position 4 of the ring structure are N- and/or O-protected with protecting groups, e.g. as conventional in β-lactam chemistry, such as silyl groups, e.g. trialkylsilyl-, aryldialkylsilyl-, diarylalkylsilyl groups, e.g. in N,O-bissilylated form. The alkyl and aryl groups may be the same or different. Alkyl includes ($C_{1-4}$)alkyl, aryl includes ($C_{5-18}$)aryl, e.g. ($C_{6-12}$)aryl, such as phenyl groups. Preferred protecting groups are trialkylsilyl groups, e.g. trimethylsilyl groups.

A compound of formula III may preferably be in protected from or in the form of a salt, e.g. in the form of a salt.

A compound of formula III in the form of a salt may be prepared e.g. as convenional in β-lactam chemistry, e.g. by addition to a salt forming agent to a mixture of a compound of formula III in organic solvent, or, in situ in a mixture of a compound of formula IV and a compound of formula III, e.g. by addition of a salt forming agent, e.g. an amine or ammonia, to a mixture of a compound of formula III, a compound of formula IV and organic solvent. A compound of formula III in protected form, e.g. N,O-bissilylated, may be prepared e.g. as conventional, e.g. analogously to a method as conventional in β-lactam chemistry. The reaction of a compound of formula III with a compound of formula IV may be carried out in inert organic solvent. Inert organic solvent includes halogenated hydrocarbons, e.g. dichloromethane, carboxylic acid esters, e.g. ethyl acetate, butyl acetate or ketones, e.g. methyl isobutyl ketone, preferably halogentad hydrocarbons; and mixtures of individual inert organic solvent, e.g. as cited above; optionally in the presence of cosolvent, such as an alcohol, e.g. ethanol or methanol, water, or an amide, e.g. dimethylformamide, or a mixture of individual cosolvents, e.g. as cited above. Appropriate reaction temperatures include −40° to 60° C., such as −15° C. to room temperature, e.g. room temperature. Per equivalent of a compound of formula III, 1 to 1.5 equivalents of a compound of formula IV may conveniently be used. A compound of formula V obtained may be isolated and protecting groups optionally present may be splitt off, e.g. analogously to a method as conventional in β-lactam chemistry and/or a compound of formula V in the form of a salt may be converted into a compound of formula V in free form, e.g. according to a method as conventional. A compound of formula V may be obtained in impure form.

A compound of formula V, e.g. in free form or in the form of a hydrate, e.g. in the form of a sesquihydrate, may e.g. also be produced according to a method as conventional, e.g. by acylating a compound of formula III, e.g. in free form, protected form or in the form of a salt, e.g. as described above, with a 4-halo-3-oxo-2-(aryl-or alk)-oxycarbonyl-methoxyimino butyric acid, wherein aryl and alkyl may have the meaning as described above for R in a compound of formula IV or V, and wherein halo denotes halogenide, preferably bromo, chloro, e.g. chloro; e.g. in an activated form, e.g. activated via Vilsmeier formation, or activated in the form of a halogenide, e.g. bromide, chloride, such as chloride, e.g. prepared by reacting 4-halo-3-oxo-2-((aryl-or alk)-oxycarbonyl-methoxyimino butyric acid, with a carboxylic acid halogenide forming agent, e.g. phosphorous oxychloride, e.g. without isolation of 4-halo-3-oxo-2-(aryl-or alk)-oxycarbonyl-methoxyimino butyric acid halogenide from the reaction mixture, to obtain 7-(2-(chloromethylcarbonyl)-2-(Z)((aryl-or alk)-oxycarbonyl)-methoxyimino)-acetamido)-3-vinyl-ceph-3-em-4-carboxylic acid, wherein the carboxylic group in position 4 of the ring system is free, or protected, or in the form of a salt; which is reacted, e.g. without isolation from the reaction mixture obtained, with thiourea to obtain a compound of formula V wherein the carboxylic acid group in position 4 of the ring system is free, or protected, or in the form of a salt and optionally splitting off protecting groups to obtain a compound of formula V and/or converting a salt of a compound of formula V into a free form of a compound of formula V, e.g. according or analogously to a method as conventional. A compound of formula V may be obtained in impure form.

Purification of a compound of formula V is difficult, e.g. because of its poor solubility in common organic solvents, e.g. halogenated hydrocarbons, ketones or esters.

We have now surprisingly found a simple and effective process for the purification of a compound of formula V via formation of a special novel salt.

In another aspect the present invention provides 7-[2-(aminothiazol-4-yl)-2-((aryl-or alk)-oxycarbonylmethoxyimino)acetamido]-3-vinyl-3-ceph-3-em-4-carboxylic acid, e.g. a compound of formula V, in the form of a salt with tert.octylamine of formula:

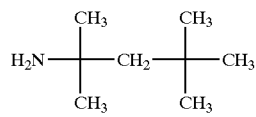

A compound according to the present invention, i.e. (7-[2-(aminothiazol-4-yl)-2-((aryl-or alk)-oxycarbonyl-methoxyimino)acetamido]-3-vinyl-3-ceph-3-em-4-carboxylic acid, e.g. a compound of formula V, in the form of a salt with tert.octylamine may be prepared as follows:

A compound of formula V may be reacted with tert.octylamine, e.g. a compound of formula V may be dissolved in the presence of tert.octylamine in organic solvent, for example, alcohols, e.g. methanol, e.g. in a mixture with co-solvents, e.g. in solvent as used in a reaction between a compound of formula III and a compound of formula IV in the presence of alcohol. The amount of the organic solvent, e.g. alcohol, should be sufficient that a solution is obtained. A non-solvent, for example an ester, e.g. ethyl acetate or butyl acetate, a ketone, e.g. methyl isobutyl ketone, or a chlorinated hydrocarbon e.g. dichloromethane, or a mixture of individual solvents, e.g. as mentioned above, may be added to the solution obtained and a compound according to the present invention may crystallise. Crystallisation may be supported by distilling off (parts of) the previously added alcohol. The amount of tert.octylamine is not critical. Preferably between one and two equivalents of tert.octylamine per equivalent of compound of formula V may be used. A compound according to the present invention may be isolated, e.g. according to a method as conventional, e.g. by filtration, centrifugation. A non-solvent is understood to be a solvent (system) in which on addition to a solvent system the solubility of the compound is lowered.

In another aspect the present invention provides a process for the production of a 7-[2-(aminothiazol-4-yl)-2-((aryl-or alk)-oxycarbonylmethoxyimino)acetamido]-3-vinyl-3-ceph-3-em-4-carboxylic acid, e.g. a compound of formula V, in the form of a salt with tert.octylamine, comprising reacting 7-[2-(aminothiazol-4-yl)-2-((aryl-or alk)-oxycarbonylmethoxyimino)acetamido]-3-vinyl-3-ceph-3-em-4-carboxylic acid with tert.octylamine and isolating a 7-[2-(aminothiazol-4-yl)-2-((aryl-or alk)-oxycarbonylmethoxyimino)acetamido]-3-vinyl-3-ceph-3-em-4-carboxylic acid, e.g. a compound of formula V, in the form of a salt with tert.octylamine, e.g. in crystalline form.

A compound of formula V in the form of a salt with tert.octylamine may be prepared without isolation of a compound of formula V from its production reaction mixture, e.g. in a one pot reaction.

In the production of a compound of formula V via reaction of a compound of formula III with a compound of formula IV, e.g. as described above, a compound of formula IV may be replaced by an activated ester other than described above, or via an amide of 2-(2-amino-4-thiazolyl)-(Z)-2-((aryl-or alk)-oxycarbonyl)methoxyimino)acetic acid, e.g. of formula

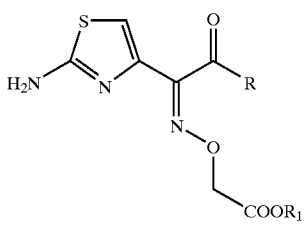

wherein $R_1$ is —O—P$^+$(Ph)$_3$Cl$^-$, —O—P(S)(OR$_4$)$_2$, —O-benztriazol-1-yl, —S—(2-methyl-thiadiazol-5-yl), —S—O—CH=N$^+$(CH$_3$)$_2$Cl$^{31}$ or -benztriazol-1-yl-3-oxide.

Such esters are known and may be prepared as conventional or analogously to a method as conventional.

In another aspect the present invention provides a process for the production of compound of formula V in the form of a salt with tert-octylamine comprising the steps (i) reacting a compound of formula III in free form, protected form or in the form of a salt with an activated ester of 2-(2-amino-4-thiazolyl)-(Z)-2-((aryl-or alk)-oxycarbonyl)-methoxyimino)acetic acid, e.g. and optionally splitting off protecting groups, and optionally converting a compound of formula V in salt form to obtain a compound of formula V in free form, and (ii) reacting a compound of formula V in free form obtained in step (i) with tert.-octylamine; e.g. wherein in step (i) an activated ester of 2-(2-amino-4-thiazolyl)-(Z)-2-((aryl-or alk)-oxycarbonyl)-methoxyimino) acetic acid is used without isolation from its production process, e.g. wherein steps (i) and (ii) are carried out in a one-pot reaction.

In another aspect the present invention provides a process for the production of compound of formula V in the form of a salt with tert-octylamine comprising the steps (i) acylating a compound of formula III, e.g. in free form, protected form or in the form of a salt with a 4-halo-3-oxo-2-(aryl-or alk)-oxycarbonyl-methoxyimino butyric acid, wherein halo denotes halogenide, in an activated form, to obtain a 7-(2-(chloromethylcarbonyl)-2-((Z)((aryl-or alk)-oxycarbonyl)methoxyimino)-acetamido)-3-vinyl-ceph-3-em-4-carboxylic acid, e.g. in free form or in salt form, wherein the carboxylic acid group in position 4 of the ring system is protected or unprotected, (ii) reacting a 7-(2-(chloromethylcarbonyl)-2-((Z)((aryl-or alk)-oxycarbonyl)methoxyimino)-acetamido)-3-vinyl-ceph-3-em-4-carboxylic acid obtained in step (I) with thiourea, e.g. and optionally splitting off protecting groups to obtain a compound of formula V, e.g. in free form or in salt form, and optionally converting a compound of formula V in the form of a salt to obtain a compound of formula V in free form, and (iii) reacting a compound of formula V in free form obtained in step (i) with tert.-octylamine; e.g. wherein in step (i) 4-halo-3-oxo-2-(aryl-or alk)-oxycarbonyl-methoxyimino butyric acid in an activated form is used without isolation from its activation process, e.g. wherein steps (i), (ii) and (iii) are carried out in a one-pot reaction.

A compound according to the present invention may be obtained in highly pure form, e.g. higher than 98.9%, e.g. from 98.9 up to 99.5% and more, e.g. 99.3% and more, e.g. directly from a reaction mixture between a compound of formula III and a compound of formula IV or directly from a reaction mixture of 7-(2-(chloromethylcarbonyl)-2-((Z) ((aryl-or alk)-oxycarbonyl)methoxyimino)-acetamido)-3-vinyl-ceph-3-em-4-carboxylic with thiourea, e.g. without isolation of a compound of formula V. A compound of formula V may thus be produced in highly pure form and in high yields in a one pot reaction starting from a compound of formula III.

A compound of the invention may be converted into a compound of formula V, e.g. by pH adjustment of a solution thereof, e.g. an aqueous solution, e.g. as conventional, e.g. by addition of an acid, to obtain a compound of formula V in highly pure form (e.g. corresponding to the purity of a compound of the present invention, or even higher). A compound of formula V may be converted into 7-[2-(aminothiazol-4-yl)-2-(carboxymethoxyimino)acetamido]-3-vinyl-3-ceph-3-em-4-carboxylic acid, e.g. cefixime, e.g. in free form, e.g. in the form of a trihydrate, e.g. as conventional, e.g. by saponification of the ester group attached to the carbonyliminomethoxy group to obtain the free carboxylic acid, e.g. by a method as conventional.

A compound according to the present invention may also directly be converted into 7-[2-(aminothiazol-4-yl)-2-(carboxymethoxyimino)acetamido]-3-vinyl-3-ceph-3-em-4-carboxylic acid, e.g. cefixime, e.g. in free form, e.g. in the form of a trihydrate, in a one pot reaction by saponification of the ester group attached to the carbonyliminomethoxy group to obtain the free carboxylic acid and pH adjustment of the reaction mixture. Conversion may be carried out as follows:

A compound according to the present invention may be dissolved in water. The pH of the solution obtained may be adjusted to a basic value, e.g. higher than 8, e.g. by addition of a base, e.g. alkali hydoxide, carbonate. Saponification may be terminated within short time. The pH of a solution obtained may be adjusted to around 7, e.g. by addition of an acid, e.g. an organic or inorganic acid, or both. 7-[2-(aminothiazol-4-yl)-2-(carboxymethoxyimino)-acetamido]-3-vinyl-3-ceph-3-em-4-carboxylic acid, e.g. cefixime, e.g. in free form, e.g. in the form of a trihydrate may crystallise, e.g. upon addition of a non-solvent, e.g. alcohols such as ethanol and may be isolated, e.g. as conventional, e.g. by filtration, centrifugation. Purity of 7-[2-(aminothiazol-4-yl)-2-(carboxymethoxyimino)-acetamido]-3-vinyl-3-ceph-3-em-4-carboxylic acid thus obtained may be corresponding to that of a compound of the present invention or even higher, e.g. higher than 98.9%, e.g. between 98.9 and 99.5%, e.g. 99.3%.

In another aspect the present invention provides a process for the production of cefixime comprising converting a compound of formula V in the form of a salt with tert.octylamine into 7-[2-(aminothiazol-4-yl)-2-(Z) (carboxymethoxyimino)acetamido]-3-vinyl-3-ceph-3-em-4-carboxylic acid, e.g. a compound of formula II, e.g. cefixime, e.g. in the form of a hydrate, such as a trihydrate, e.g. wherein a compound of formula V is prepared as described herein.

Formation of a compound of the present invention, which may be crystalline, may be highly useful, e.g. it may have a high purification effect on the purity of a compound of formula V. A compound of formula V in the form of a salt with tert.octylamine may surprisingly be prepared in a one pot reaction starting from a compound of formula III, e.g. according to a novel method for the production of a compound of formula V via a novel compound of formula IV or according to a known process for the production of a compound of formula V. A compound of formula V may be converted into cefixime having a purity of up to 99% and more.

In another aspect the present invention provides a tert.-octylamine salt of 7-[2-(aminothiazol-4-yl)-2-((aryl-or alk)-oxycarbonylmethoxyimino)-acet-amido]-3-vinyl-3-ceph-3-em-4-carboxylic acid of formula

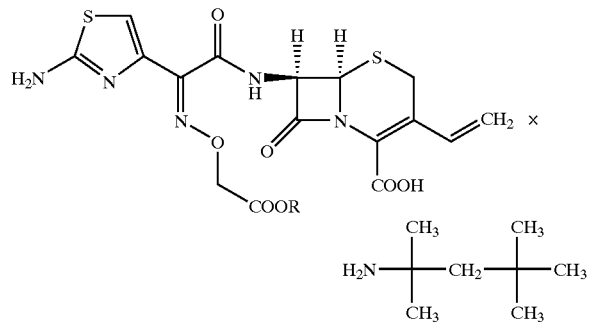

In another aspect the present invention provides the use of a compound of the present invention in the production of cefixime.

The following examples are intended to illustrate the invention without limiting its scope All temperatures are given in degrees Celsius.

EXAMPLE 1

2 g of 7-{2-[(2-aminothiazol)-4-yl]-2-[(Z)(methoxycarbonyl)methoxyimino]acetamido}-3-vinyl-ceph-3-em-4-carboxylic acid and 0.7 g of tert. octylamine are dissolved in 50 ml of methanol and the mixture obtained is treated with 0.2 g of activated carbon. The activated carbon is filtrated off. To the filtrate obtained 0.7 g of tert. octylamine and 200 ml of dichloromethane are added. From the mixture obtained the solvent is evaporated off. At the same time 400 ml of fresh dichloromethane are added to the mixture such that the volume of the mixture is kept roughly constant. 7-{2-[(2-aminothiazol)-4-yl]-2-[(Z)(methoxycarbonyl)methoxyimino]acetamido}-3-vinyl-ceph-3-em-4-carboxylic acid in the form of salt with tert.octylamine crystallizes, is filtrated off and dried.

Yield: 2 g Content (HPLC): 98.0% (as a salt) Water content (KF): 1.8% Melting point: from 160° C. (decomp.)

$^1$H-NMR: Bruker AC300 (300 MHz); 10 mg in 0.6 ml DMSO-$d_6$, with 32 scans at a digital resolution of 0.2 Hz/point:

| No. | δ [ppm] | number | Mult. | J [Hz] | association |
|---|---|---|---|---|---|
| 1 | 9.50 | 1 | br (d) | | NH |
| 2 | 8.20 | 3 | br | | $NH_3$ |
| 3 | 7.28 | 2 | s | | $NH_2$ |
| 4 | 7.10 | 1 | dd | 11, 18 | —CH═$CH_2$ |
| 5 | 6.77 | 1 | s | | S—CH═ |
| 6 | 5.60 | 1 | br m | | H(7) |
| 7 | 5.16 | 1 | d | 17 | —CH═$CH_2$ |
| 8 | 5.07 | 1 | d | 5 | H(6) |
| 9 | 4.93 | 1 | d | 11 | —CH═$CH_2$ |
| 10 | 4.67 | 2 | s | | O—$CH_2$ |
| 11 | 3.66 | 3 | s | | $CH_3$ |
| 12 | 3.54 | 1 | AB d | 17 | H(2) |
| 13 | 3.47 | 1 | AB d | 17 | H(2) |
| 14 | 1.60 | 2 | s | | $CH_2$ |
| 15 | 1.30 | 6 | s | | $CH_3$ |
| 16 | 0.96 | 9 | s | | t-Bu |

EXAMPLE 2

2.1.A. To a mixture of 32.3 g of 2-(2-amino-4-thiazolyl)-(Z)-2-(methoxycarbonylmethoxyimino)acetic acid with 1250 ml of dichloromethane, 39.5 g of triphenylphosphine and 50 g of 2,2'-benzothiazolyl disulphide are added and the mixture is stirred for 5 minutes at 20°. To the mixture obtained 25 g of triethylamine are added dropwise.

2.1.B. To a mixture obtained in step 2.1.A. 22 g of 7-amino-3-vinyl-ceph-3-em-4-carboxylic acid, 12.5 ml of water and 10 g of triethylamine are added and the mixture obtained is stirred for ca. 2 hours at 30–35°. After completion of the reaction (HPLC determination) a solution of 25 g of tert.-octylamine in 50 ml of dichloromethane is added dropwise to the mixture obtained. A solution is obtained from which 7-{2-[(2-aminothiazol)-4-yl]-2-[(Z)(methoxycarbonyl)methoxyimino]acetamido}-3-vinyl-ceph-3-em-4-carboxylic acid in the form of a salt with tert.octylamine salt crystallizes, which is filtrated off and dried.

Yield: 36 g Content (HPLC): 98.6% Σ By-products (HPLC): 1.2% of area 2.2. 5 g of 7-{2-[(2-aminothiazol)-4-yl]-2-[(Z)(methoxycarbonyl)methoxyimino]acetamido}-3-vinyl-ceph-3-em-4-carboxylic acid in the form of a salt with tert.octylamine are dissolved in 100 ml of water and cooled to 0°. To the cloudy solution is is added 7.7 ml of 5 M sodium hydroxide solution. The resulting clear solution is neutralised with conc. hydrochloric acid and 0.08 g of ascorbic acid and 1.75 g of activated carbon are added under stirring. Activated carbon is filtrated off, 50 ml of water and 100 ml of ethanol are added to the filtrate obtained and the pH is adjusted to 3.0 with 6 N hydrochloric acid. 7-{2-[(2-aminothiazol)-4-yl]-2-[(Z)(methoxycarbonyl)methoxyimino]acetamido}-3-vinyl-ceph-3-em-4-carboxylic acid crystallises, the pH of the suspension obtained is adjusted to 3.5 and the suspension is chilled for an additonal hour in an icebath. 7-{2-[(2-aminothiazol)-4-yl]-2-[(Z)(methoxycarbonyl)methoxyimino]acetamido}-3-vinyl-ceph-3-em-4-carboxylic acid crystallises in the form of a trihydrate is filtrated off and dried.

Yield: 3.59 g in the form of a white crystalline powder Content HPLC (anhydrous): 98.2% HPLC purity: 98.9% of area

EXAMPLE 3

3.1.A. 3.44 g of phosphorus oxychloride are added dropwise at −10° to a solution of 3.28 g of dimethylformamide in 16 ml of tetrahydrofuran and the mixture otained is stirred for ca. 30 minutes. To the mixture obtained 5.32 g of 4-chloro-2-(methoxycarbonyl)methoxyimino]-3-oxobutyric acid are added and the mixture obtained is stirred for ca. one hour at −10°.

3.1.B. To a mixture of 4.40 g of 7-amino-3-vinyl-ceph-3-em-4-carboxylic acid in 40 ml of dichloromethane are added 8.0 g of N,O-bistrimethylsilyl acetamide and the mixture obtained is stirred at 20° for ca. 4 hours and cooled to −10°. The mixture prepared according to 3.1.A. is added dropwise at −10° C. and the mixture obtained is stirred for ca. 90 minutes at −10°. The mixture obtained is added to a solution of 5.92 g of thiourea in 30 ml of water and the pH is adjusted to 5.5 with solid sodium hydrogen carbonate. The mixture obtained is stirred for ca. 2 hours at 20° maintaining a pH of 5.5 by addition of solid sodium hydrogen carbonate and treated with 100 ml of water. A two-phase system is obtained and the phases are separated. The aqueous phase is mixed with 200 ml of dichloromethane and 160 ml of methanol, and the pH of the mixture is adjusted to 2.5 with 6 N hydrochloric acid. A two-phase system is obtained and the phases are separated. The aqueous phase is extracted with dichloromethane. The organic phase is concentrated in vacuo and a solution of 3.2 g of tert.octylamine in 10 ml of dichloromethane is added dropwise to the residue obtained. 200 ml of dichloromethane are added to the mixture obtained. 7-{2-[(2-aminothiazol)-4-yl]-2-[(Z)(methoxycarbonyl)methoxyimino]acetamido}-3-vinyl-ceph-3-em-4-carboxylic acid in the form of a salt with tert.octylamine crystallizes, is filtrated off and dried.

Yield: 5.38 g Content: 90.8% HPLC purity: 95.3% of area 3.2. From 2.0 g 7-{2-[(2-aminothiazol)-4-yl]-2[(Z)(methoxycarbonyl)methoxyimino]-acetamido}-3-vinyl-ceph-3-em-4-carboxylic acid in the form of a salt with tert.octylamine obtained as described under 3.1.B., 1.24 g of 7-{-2-[(2-aminothiazol)-4-yl]-2-[(Z)(methoxycarbonyl)-methoxyimino]acetamido}-3-vinyl-ceph-3-em-4-carboxylic acid in the form of a trihydrate are obtained analogously as described in Example 2.2. Content (HPLC) anhydrous: 96.5% in the form of a white crystalline powder HPLC purity: 99.34% of area

What is claimed is:

1. Tert-octylamine salt of 7-[2-(2-aminothiazol4-yl)-2-((aryl-or alk)-oxycarbonylmethoxyimino)acetamido]-3-vinyl-3-ceph-3-em-4-carboxylic acid of formula

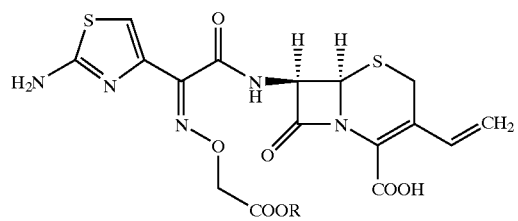

V wherein the amine group attached to the thiazolyl ring is free or protected, and wherein the tert-octylamine has the formula:

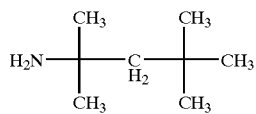

and wherein R denotes alkyl or aryl.

2. The tert-octylamine salt of a compound of formula V according to claim 1 wherein R is methyl.

3. A process for the production of a tert-octylamine salt of a compound of formula

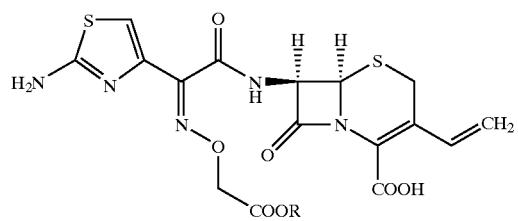

V wherein the amine group attached to the thiazolyl ring is free or protected, and wherein the tert-octylamine has the formula

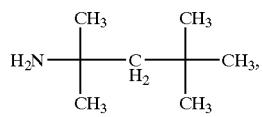

and wherein R denotes alkyl or aryl, comprising the steps
(I) reacting a compound of formula III

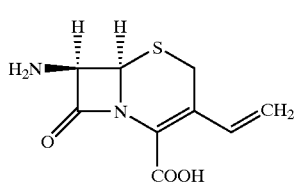

III in free form or in the form of a salt, with an activated ester of 2-(2-amino-4-thiazolyl)-(Z)-2-((aryl- or alk)-oxycarbonyl)-methoxyimino)acetic acid, to obtain a compound of formula V in free form, or in the form of a salt and converting a compound of formula V in the form of a salt into a compound of formula V in a free form, and
(II) reacting a compound of formula V in free form obtained in step (i) with tert. octylamine.

4. A process according to claim 3, wherein an activated ester of 2-(2-amino-4-thiazolyl)-(Z)-2-((aryl-or alk)-oxycarbonyl)-methoxyimino)acetic acid is used without isolation from its production process.

5. A process for the production of a tert-octylamine salt of a compound of formula

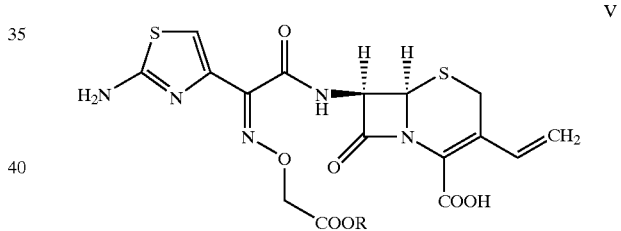

V wherein the amine group attached to the thiazolyl ring is free or protected, and wherein the tert-octylamine the tile formula

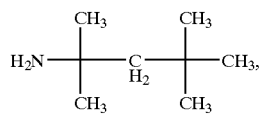

and wherein R denotes alkyl or aryl, comprising the steps
(I) acylating a compound of formula III

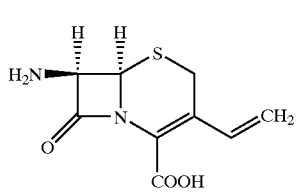

III in free form or salt form, with an activated form of 4-halo-2-[((aryl- or alk)oxycarbonyl)methoxyimino]-

3-oxo-butyric acid, to obtain a 7-(2-(halomethylcarbonyl)-2-((Z)(aryl-or alk)-oxycarbonyl)methoxyimino)-acetamido)-3-vinyl-ceph-3-em-4-carboxylic acid in free form, wherein the carboxylic acid group in position 4 of the ring system is unprotected, or in the form of a salt, and (II) reacting the 7-(2-(halomethylcarbonyl)-2-((Z)(aryl-or alk)-oxycarbonyl)methoxyimino)-acetamido)-3-vinyl-ceph-3-em-4-carboxylic acid in free form, wherein the carboxylic acid group in position 4 of the ring system is unprotected, or in the form of a salt, as obtained in step (i), with thiourea to obtain a compound of formula V in free form, or in the form of a salt and converting a salt of a compound of formula V into a free form of a compound of formula V, and (III) reacting a compound of formula V obtained in step (ii) with tert.octylamine.

6. The process according to claim 5 where halo is chloro.

7. A process according to claim 5, wherein in step (i) 4-halo-3-oxo-2-(aryl-or alk)-oxycarbonyl-methoxyimino butyric acid in an activated form is used without isolation from its activation production process.

8. A process for the production of a tert-octylamine salt of a compound of formula

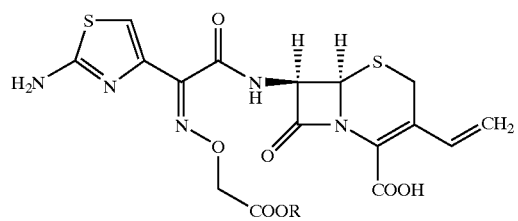

V wherein the amine group attached to the thiazolyl ring is free or protected, and wherein the tert-octylamine has the formula:

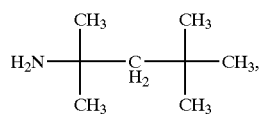

and wherein R denote, alkyl or aryl, comprising the steps (1) reacting a compound of formula III

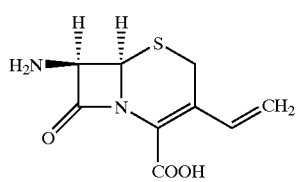

III in protected form, with an activated ester of 2-(2-amino-4-thiazolyl)-(Z)-2-((aryl- or alk)-oxycarbonyl)-methoxyimino)acetic acid, to obtain a compound of formula V, in protected form, and splitting off protecting groups, and (ii) reacting a compound of formula V in free form obtained in step (i) with tert. octylamine as defined above.

9. A process according to claim 8, wherein an activated ester of 2-(2-amino-4-thiazolyl)-(Z)-2-((aryl-or alk)-oxycarbonyl)-methoxyimino)acetic acid is used without isolation from its production process.

10. A process for the production of a tert-octylamine salt of a compound of formula

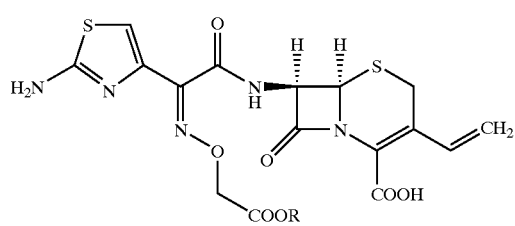

V wherein the amine group attached to the thiazolyl ring is free or protected, and wherein the tert-octylamine has the formula

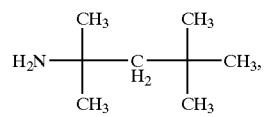

and wherein R denotes alkyl or aryl, comprising the steps (i) acylating a compound of formula III

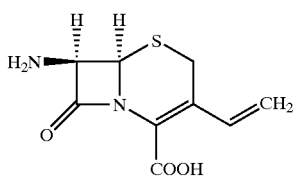

III in protected form, with an activated form of 4-halo-2-[((aryl- or alk)oxycarbonyl)methoxyimino]-3-oxo-butyric acid, to obtain a 7-(2-(halomethylcarbonyl)-2-((Z)((aryl-or alk)-oxycarbonyl)methoxyimino)-acetamido)-3-vinyl-ceph-3-em-4-carboxylic acid, wherein the carboxylic acid group in position 4 of the ring system is protected, and (ii) reacting the 7-(2-(halomethylcarbonyl)-2-((Z)((aryl-or alk)-oxycarbonyl)methoxyimino)-acetamido)-3-vinyl-ceph-3-em-4-carboxylic acid wherein the carboxylic acid group in position 4 of the ring system is protected as obtained in step (i), with thiourea to obtain a compound of formula V as defined in claim 1 wherein the carboxylic acid group in position 4 is protected, and splitting off the protecting group, and (iii) reacting a compound of formula V obtained in step (ii) with tert.octylamine.

11. A process according to claim 10, wherein in step (i) 4-halo-3-oxo-2-(aryl -or alk)-oxycarbonyl-methoxyimino butyric acid in an activated form is used without isolation from its activation production process.

12. The process according to claim 10 wherein halo is chloro.

13. A process for the preparation of a product which is the tert-octylamine salt of a compound of formula V:

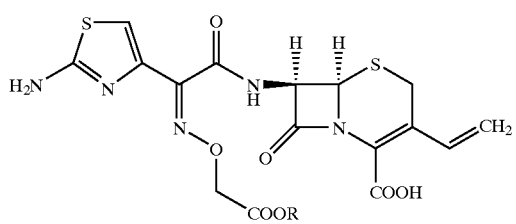

V wherein the amine group attached to the thiazolyl ring is free or protected, and wherein the tert-octylamine has the formula:

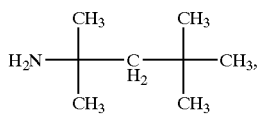

and wherein R denotes alkyl or aryl, comprising the steps (i) reacting a compound of formula V, above, (ii) with tert-octylamine as defined above, in solution with an organic solvent; then (iii) followed by addition of a non-solvent for the product to crystallize the product.

* * * * *

UNITED STATES PATENT AND TRADEMARK OFFICE
CERTIFICATE OF CORRECTION

PATENT NO. : 6,825,345 B2
DATED : November 30, 2004
INVENTOR(S) : Decristoforo et al.

It is certified that error appears in the above-identified patent and that said Letters Patent is hereby corrected as shown below:

Column 9,
Line 23, should read -- 1. Tert-octylamine salt of 7-[2-(2-aminothiazol-4-yl)-2- --.

Column 10,
Line 45, should read -- or protected, and wherein the tert-octylamine has the for- --.

Column 11,
Line 46, should read -- and wherein R denotes alkyl or aryl, comprising the steps --.

Signed and Sealed this

Eleventh Day of October, 2005

JON W. DUDAS
*Director of the United States Patent and Trademark Office*